United States Patent
Bao et al.

(10) Patent No.: US 11,963,806 B2
(45) Date of Patent: Apr. 23, 2024

(54) SYSTEMS AND METHODS FOR A PARAMETER ADJUSTMENT OF A MULTI-ENERGY COMPUTED TOMOGRAPH DEVICE

(71) Applicant: SHANGHAI UNITED IMAGING HEALTHCARE CO., LTD., Shanghai (CN)

(72) Inventors: Yuan Bao, Shanghai (CN); Meili Yang, Shanghai (CN); Jianwei Fu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 296 days.

(21) Appl. No.: 17/645,999

(22) Filed: Dec. 27, 2021

(65) Prior Publication Data

US 2022/0211337 A1 Jul. 7, 2022

(30) Foreign Application Priority Data

Dec. 29, 2020 (CN) .......................... 202011604727.2

(51) Int. Cl.
*A61B 6/00* (2006.01)
*A61B 6/03* (2006.01)
*A61B 6/40* (2024.01)

(52) U.S. Cl.
CPC ............ *A61B 6/4035* (2013.01); *A61B 6/032* (2013.01); *A61B 6/482* (2013.01); *A61B 6/54* (2013.01)

(58) Field of Classification Search
CPC ....... A61B 6/4035; A61B 6/032; A61B 6/482; A61B 6/54; A61B 6/06; A61B 6/48
See application file for complete search history.

(56) References Cited

U.S. PATENT DOCUMENTS

| | | | |
|---|---|---|---|
| 6,870,898 B1 * | 3/2005 | von der Haar | A61B 6/032 378/97 |
| 2003/0123614 A1 * | 7/2003 | Silver | G06T 11/005 378/146 |
| 2009/0175562 A1 * | 7/2009 | Pan | A61B 6/5288 382/312 |

OTHER PUBLICATIONS

Fuchs et al., "Fast vol. scanning approaches by X-ray-computed tomography", Proceedings of the IEEE, vol. 91, Issue 10, pp. 1492-1502. (Year: 2003).*

* cited by examiner

*Primary Examiner* — Kiho Kim
(74) *Attorney, Agent, or Firm* — METIS IP LLC

(57) ABSTRACT

Systems and methods for a parameter adjustment of a multi-energy computed tomography (CT) device is provided. The systems and methods may obtain, by at least one processor, a parameter set associated with a scan to be performed using a multi-energy CT device. The parameter set may include multiple scanning parameters and multiple reconstruction parameters. The systems and methods may also determine, by the at least one processor, a maximum pitch associated with the scan based on a correlation relationship and the parameter set. The correlation relationship may describe a correlation between a pitch of the multi-energy CT device and the parameter set.

20 Claims, 10 Drawing Sheets

500

```
┌─────────────────────────────────────────────────────────────┐
│ Obtaining, by at least one processor, a parameter set        │   501
│ associated with a scan to be performed using a multi-energy  │ ⌇⌇
│ computed tomography (CT) device                              │
└─────────────────────────────────────────────────────────────┘
                              │
                              ▼
┌─────────────────────────────────────────────────────────────┐
│ Determining, by the at least one processor, a maximum pitch  │   503
│ based on a correlation relationship and the parameter set    │ ⌇⌇
└─────────────────────────────────────────────────────────────┘
```

FIG. 5

SYSTEMS AND METHODS FOR A PARAMETER ADJUSTMENT OF A MULTI-ENERGY COMPUTED TOMOGRAPH DEVICE

CROSS-REFERENCE TO RELATED APPLICATIONS

This application claims priority of Chinese Patent Application No. 202011604727.2, filed on Dec. 29, 2020, the contents of which are hereby incorporated by reference.

TECHNICAL FIELD

The present disclosure generally relates to imaging technology, and more particularly, systems and methods for a parameter adjustment of a multi-energy computed tomography (CT) device.

BACKGROUND

With the development of the radiation (e.g., X-rays) detector and imaging system, the multi-energy CT device (e.g., a dual-energy CT device) has been widely used. Compared with a traditional single-energy CT device, a dual-energy CT device can quantify iodine or calcium components in tissues by utilizing material decomposition imaging. For example, the distribution of the iodine components determined by the material decomposition imaging may be depicted with a pseudo-color to obtain an iodine map, which can reflect the iodine concentration value in a lesion and evaluate the degree of tumor vascularization. The dual-energy CT device may not only provide morphological information of a tumor but also be used for diagnosis (e.g., differential diagnosis) of a lesion according to different iodine contents of benign and malignant tumors. In addition, the dual-energy CT device may generate images of a relatively high energy level and images of a relatively low energy level, which can improve the image contrast, reduce metal and hardening artifacts, and/or increase the display rate of the lesion. Accordingly, the dual-energy CT device is of great significance in the field of clinical diagnosis.

Generally, before a scan of a patient using a multi-energy CT device is performed, a user (e.g., medical personnel, such as a doctor or a technician) may need to determine various parameters according to the specific situation of the patient and the user experience. In addition, when one parameter of the various parameters changes, other parameters may need to be manually adjusted accordingly, resulting in undesirable factors in such imaging including, e.g., inter-user variations, low imaging efficiency and/or accuracy, or the like, or a combination thereof. Therefore, it is desirable to provide systems and methods for a parameter adjustment of the multi-energy CT device, thereby improving the efficiency and accuracy of imaging using the multi-energy CT device.

SUMMARY

In an aspect of the present disclosure, a system is provided. The system may include at least one storage device including a set of instructions, and at least one processor configured to communicate with the at least one storage device. When executing the set of instructions, the at least one processor may be configured to direct the system to perform the following operations. The operations may include obtaining, by the at least one processor, a parameter set associated with a scan to be performed using a multi-energy computed tomography (CT) device. The parameter set may include multiple scanning parameters and multiple reconstruction parameters. The operations may also include determining, by the at least one processor, a maximum pitch associated with the scan based on a correlation relationship and the parameter set. The correlation relationship may describe a correlation between a pitch of the multi-energy CT device and the parameter set.

In some embodiments, the multi-energy CT device may include a gantry, a collimator, a radiation source, and an isocenter. The scan to be performed may include a plurality of sub-scans, at least two consecutive sub-scans of the plurality of sub-scans being at different energy levels. The multiple scanning parameters may include a rotation velocity of the gantry, a collimation width of the collimator, a current time product of a sub-scan at an energy level, a switch time between the two consecutive sub-scans, a scan angle of a sub-scan at the energy level, and a distance between the radiation source and the isocenter (SID).

In some embodiments, the multiple reconstruction parameters may include a reconstruction field of view (FOV), a reconstruction range of the reconstruction FOV, a reconstruction center, a reconstruction image thickness, and a reconstruction angle of a sub-scan at the energy level.

In some embodiments, the correlation relationship may include at least one of the following the pitch negatively correlates with the reconstruction FOV; the pitch s negatively correlates with the reconstruction image thickness; the pitch negatively correlates with the reconstruction angle of a sub-scan at an energy level; the pitch may positively correlate with the collimation width; the pitch negatively correlates with the scan angle of a sub-scan at the energy level; the pitch may positively correlate with the SID; the pitch negatively correlates with the rotation velocity; or the pitch negatively correlates with the switch time associated with the two consecutive sub-scans.

In some embodiments, the scan to be performed may include a plurality of sub-scans. Two consecutive sub-scans of the plurality of sub-scans may include a first sub-scan and a second sub-scan. The operations may further include obtaining a first current time product of the first sub-scan; obtaining a preset ratio of a first CT dose index (CTDI) of the first sub-scan to a second CTDI of the second sub-scan; and determining a second current time product of the second sub-scan based on the first current time product and the preset ratio.

In some embodiments, the first CTDI may positively correlate with the first current time product, and the second CTDI may positively correlate with the second current time product.

In some embodiments, the operations may further include determining a switch time between the two consecutive sub-scans based on the first current time product and the second current time product. The switch time may positively correlate with a difference between the first current time product and the second time product.

In some embodiments, the operations may further include causing the multi-energy CT device to perform the scan according to the scan parameter set and the maximum pitch.

In some embodiments, the performing the scan according to the scan parameter set and the maximum value of the pitch may include determining a target pitch based on the maximum pitch and a target scan speed; adjusting at least one parameter of the parameter set based on the target pitch and the correlation relationship; and causing the multi-energy CT device to perform the scan according to the adjusted parameter set and the target pitch. The target pitch may be less than the maximum pitch.

In another aspect of the present disclosure, a system for parameter adjustment is provided. The system may include at least one storage device including a set of instructions and at least one processor configured to communicate with the at least one storage device. When executing the set of instructions, the at least one processor may be configured to direct the system to perform the following operations. The operations may include obtaining, by the at least one processor, a parameter correlation set associated with a scan to be performed using a multi-energy computed tomography (CT) device. The parameter correlation set may include multiple scanning parameters and multiple reconstruction parameters. The operations may also include updating, by the at least one processor, at least one parameter of the parameter correlation set. The operations may also include updating, by the at least one processor, one or more of remaining parameters of the parameter set correlation set based on the updated at least one parameter according to a sufficiency need. The operations may further include causing, by the at least one processor, the multi-energy CT device to perform the scan according to the updated parameter correlation set.

In some embodiments, the multi-energy CT device may include a gantry, a collimator, a radiation source, and an isocenter. The scan to be performed may include a plurality of sub-scans. At least two consecutive sub-scans of the plurality of sub-scans may be at different energy levels. The multiple scanning parameters may include a pitch of the multi-energy CT device, a rotation velocity of the gantry, a collimation width of the collimator, a current time product of a sub-scan at an energy level, a switch time between the two consecutive sub-scans, a scan angle of a sub-scan at the energy level, and a distance between the radiation source and the isocenter (SID).

In some embodiments, the multiple reconstruction parameters may include a reconstruction field of view (FOV), a reconstruction range of the reconstruction FOV, a reconstruction center, a reconstruction image thickness, and a reconstruction angle of a sub-scan at the energy level.

In some embodiments, the updating, by the at least one processor, one or more remaining parameters of the parameter set correlation set based on the updated at least one parameter according to a data efficiency need may include determining a first distance and a second distance based on the updated at least one parameter and the remaining parameters of the parameter correlation set; and updating the one or more of remaining parameters under a condition that the first distance being less than or equal to the second distance. The first distance may refer to an interval between two consecutive sub-scans with a same energy level, and the second distance may refer to a maximum interval between the two consecutive sub-scans with the same energy level.

In some embodiments, the determining a first distance and a second distance based on the updated at least one parameter and the remaining parameters of the parameter correlation set may include determining the first distance based on at least one of the scan angle of the sub-scan at the energy level, the pitch, the collimation width of the collimator, the rotation velocity of the gantry, the switch time between the two consecutive sub-scans, and a reconstruction angle of a sub-scan at the energy level; and determining the second distance based on at least one of the reconstruction FOV, the reconstruction image thickness, the SID, and the collimation width.

In some embodiments, the updating, by the at least one processor, one or more of remaining parameters of the parameter set correlation set based on the updated at least one parameter according to a data efficiency need may include updating a pitch of the multi-energy CT device based on the updated at least one parameter according to the data sufficiency need.

In some embodiments, the updating, by the at least one processor, one or more of remaining parameters of the parameter set correlation set based on the updated at least one parameter according to a data efficiency need may include updating the one or more of remaining parameters according to at least one of the following the pitch negatively correlates with the reconstruction FOV; the pitch s negatively correlates with the reconstruction image thickness; the pitch negatively correlates with the reconstruction angle of a sub-scan at an energy level; the pitch may positively correlate with the collimation width; the pitch negatively correlates with the scan angle of a sub-scan at the energy level; the pitch may positively correlate with the SID; the pitch negatively correlates with the rotation velocity; or the pitch negatively correlates with the switch time associated with the two consecutive sub-scans.

In some embodiments, the scan to be performed may include a plurality of sub-scans. Two consecutive sub-scans of the plurality of sub-scans may include a first sub-scan and a second sub-scan. The at least one processor may be further configured to direct the system to perform the operations including obtaining a first current time product of the first sub-scan; obtaining a preset ratio of a first CT dose index (CTDI) of the first sub-scan to a second CTDI of the second sub-scan; and determining a second current time product of the second sub-scan based on the first current time product and the preset ratio.

In some embodiments, the first CTDI may positively correlate with the first current time product, and the second CTDI may positively correlate with the second current time product.

In another aspect of the present disclosure, an interface associated with a multi-energy computed tomography (CT) device is provided. The interface may include a protocol selection area, a pitch determination icon, and a scan icon. The protocol selection area may be configured to receive a scan protocol selection instruction for selecting a target scan protocol from a plurality of scan protocols. Each of the plurality of scan protocols may include a parameter set including multiple scan parameters and multiple reconstruction parameters. The pitch determination icon may be configured to receive a maximum pitch determination instruction for determining a maximum pitch based on a target parameter set of the target scan protocol and a correlation relationship. The correlation relationship may describe a correlation between a pitch of the multi-energy CT device and a parameter set of a scan protocol of the multi-energy CT device. The scan icon may be configured to receive a scan instruction for causing the multi-energy CT device to perform a target scan according to the target scan protocol and the maximum pitch.

In some embodiments, to receive a scan instruction for causing the multi-energy CT device to perform a target scan according to the target scan protocol and the maximum pitch, the scan icon may be further configured to determine whether a data sufficiency data need is satisfied; in response to determining that the data sufficiency need is satisfied, direct the multi-energy CT device to perform the scan; and in response to determining that the data sufficiency need does not satisfied, adjust one or more parameters of the parameter set and/or the pitch.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for determining a maximum pitch according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in descending order. However, the terms may be displaced by another expression if they achieve the same purpose.

Figure 2:
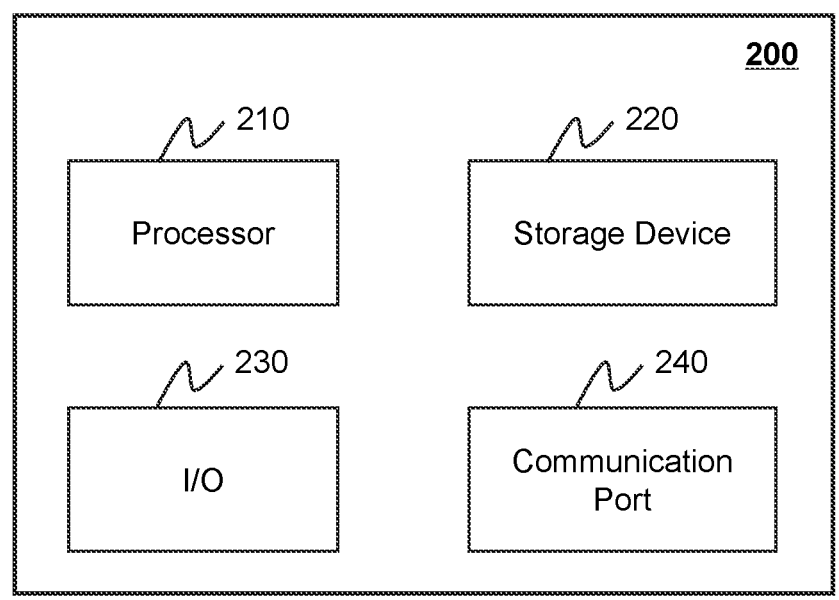
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. For example, the expression "A and/or B" includes only A, only B, or both A and B. The character "/" includes one of the associated listed terms. The term "multiple" or "a/the plurality of" in the present disclosure refers to two or more. The terms "first," "second," and "third," etc., are used to distinguish similar objects and do not represent a specific order of the objects. The term "image" in the present disclosure is used to collectively refer to image data (e.g., scan data) and/or images of various forms, including a two-dimensional (2D) image, a three-dimensional (3D) image, a four-dimensional (4D) image, etc. The terms "pixel" and "voxel" in the present disclosure are used interchangeably to refer to an element of an image. The subject may include a biological subject (e.g., a human, an animal), a non-biological subject (e.g., a phantom), etc. The term "modality" used herein broadly refers to an imaging or treatment method or technology that gathers, generates, processes, and/or analyzes imaging information of a subject or treatments the subject.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

An aspect of the present disclosure relates to systems and methods for a parameter adjustment of a multi-energy CT device. The systems and methods may obtain, by at least one processor, a parameter set associated with a scan to be performed using a multi-energy computed tomography (CT) device. The parameter set may include multiple scanning parameters and multiple reconstruction parameters. The systems and methods may determine, by the at least one processor, a maximum pitch associated with the scan based on a correlation relationship and the parameter set. The correlation relationship may include a function of the parameter set (i.e., the correlation relationship being in a form of the function of the parameter set).

Generally speaking, a scan using the multi-energy CT device may need to acquire sufficient data to satisfy a data sufficiency need. Meanwhile, it is desired that a scan takes a short amount of time (or referred to as a high or fast scan speed). The scan speed of the scan may relate to the pitch associated with the scan. As used herein, a pitch refers to a distance that a table of the multi-energy CT device travels when a gantry of the multi-energy CT device rotates a circle (i.e., 360 degrees) divided by a collimation width of the multi-energy CT device. For example, the larger the pitch is, the faster the scan speed of the scan may be. According to some embodiments of the present disclosure, before the scan of the multi-energy CT device, the systems may determine the maximum pitch associated with the scan according to a correlation relationship and a parameter set associated with the scan. Then, the systems may cause the multi-energy CT device to perform the scan based on the maximum pitch and the parameter set. In some embodiments, the systems may determine a target pitch that is less than or equal to the maximum pitch. The systems may adjust at least one parameter of the parameter set based on the target pitch and the correlation relationship. Further, the systems may cause the multi-energy CT device to perform the scan according to the adjusted parameter set and the target pitch. Accordingly, the system may determine the pitch and/or adjust the parameter(s) of the parameter set automatically, thereby reducing the amount of intervention by a user and inter-user variations, and/or improving the accuracy and efficiency of the parameter adjustment in the imaging process, which in turn may improve the imaging accuracy and/or efficiency.

Figure 1:
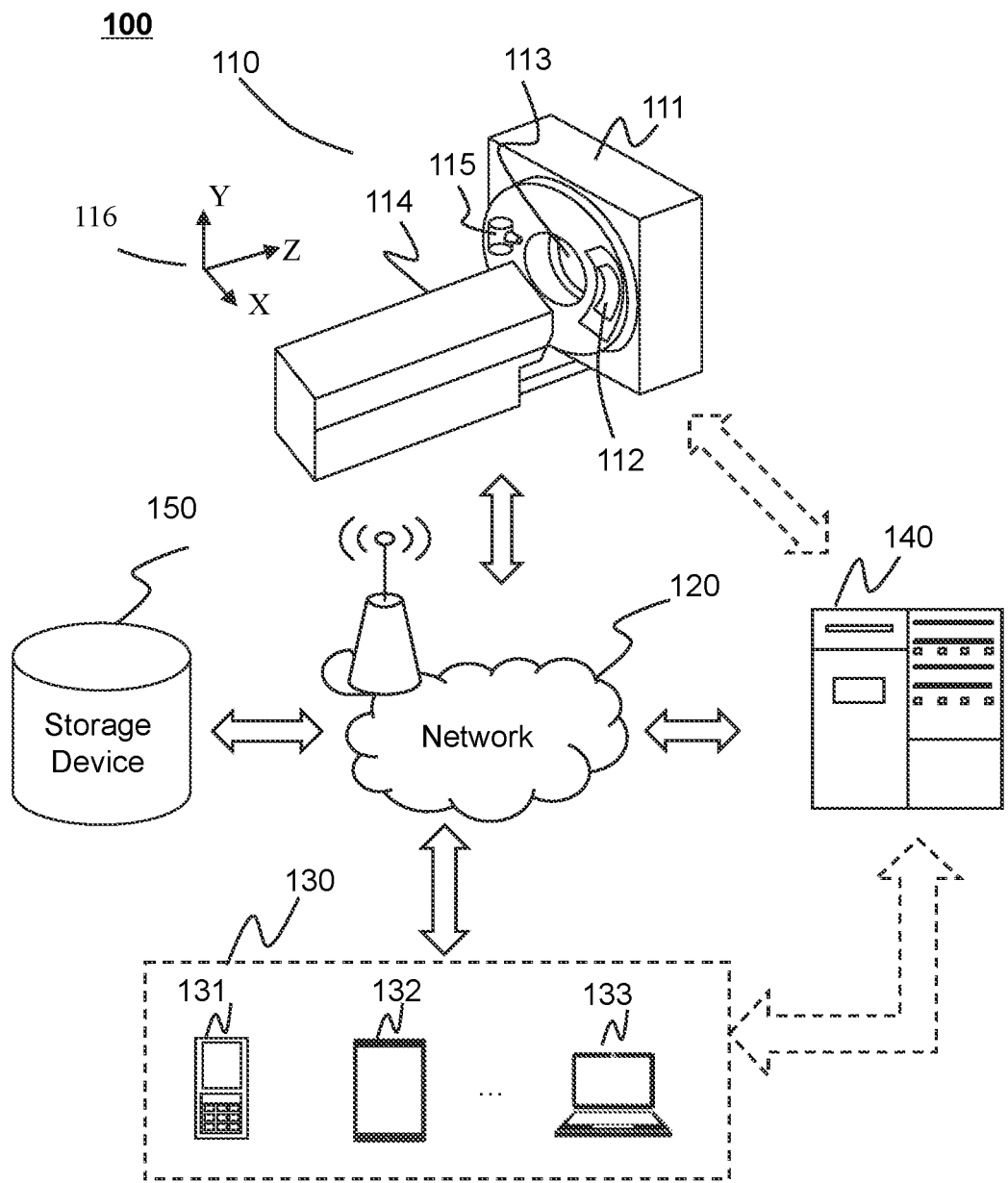
FIG. 1 is a schematic diagram illustrating an exemplary multi-energy CT system according to some embodiments of the present disclosure.

FIG. 1 is a schematic diagram illustrating an exemplary medical imaging system according to some embodiments of the present disclosure. In some embodiments, the medical imaging system may be used for non-invasive imaging, such as for disease diagnosis, treatment, and/or research purposes. In some embodiments, the medical imaging system may include a single modality system and/or a multi-modality system. The single modality system may include a multi-energy computed tomography (CT) system (e.g., a dual-energy CT device). For brevity, the term "multi-energy CT" may also be referred to as "CT" in the present disclosure. The multi-modality system may include a positron emission tomography-computed tomography (PET-CT) system, a digital subtraction angiography-computed tomography (CT-DSA) system, a computed tomography guided radiotherapy (CT guided RT) system, or the like, or any combination thereof. For illustration purposes, the medical imaging system 100 illustrated in FIG. 1 is provided with reference to a multi-energy CT system, which is not intended to limit the scope of the present disclosure.

As shown in FIG. 1, the medical imaging system 100 may include a multi-energy CT device 110, a network 120, a terminal device 130, a processing device 140, and a storage device 150. The components of the medical imaging system 100 may be connected in one or more of various ways. Mere by way of example, as illustrated in FIG. 1, the multi-energy CT device 110 may be connected to the processing device 140 through the network 120. As another example, the multi-energy CT device 110 may be connected to the processing device 140 directly (as indicated by the bi-directional arrow in dotted lines linking the multi-energy CT device 110 and the processing device 140). As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

The multi-energy CT device 110 may be configured to scan a subject, or a portion thereof, at different energy levels. Image data acquired during the scan may be reconstructed to parse components of the subject, or the portion thereof, by utilizing differences of different materials in X-ray attenuation. In some embodiments, the subject may include a biological subject (e.g., a patient) or a non-biological subject (e.g., a phantom). For example, the subject may include a specific part, organ, and/or tissue of a patient. As another example, the subject may include the head, the brain, the neck, the breast, the heart, the lung, the stomach, blood vessels, soft tissues, or the like, or any combination thereof. The term "object" or "subject" are used interchangeably in the present disclosure.

As illustrated, the multi-energy CT device 110 may include a gantry 111, a detector 112, a detecting region 113, a table 114, and a radiation source 115. The gantry 111 may support the detector 112 and the radiation source 115. The gantry 111 may rotate, for example, clockwise or counter-clockwise about an axis of rotation of the gantry 111. The radiation source 115 and/or the detector 112 may rotate together with the gantry 111. The subject may be placed on the table 114 and move together with the table 114 during a scan of the subject. The radiation source 115 may include a radiation tube. The radiation tube may be applied with a tube voltage (e.g., of a specific kilo volt (kV)) to generate a tube current for emitting a radiation beam (e.g., an X-ray beam) with a specific energy level. The specific energy level may correspond to a specific tube voltage and a specific tube current. Different tube voltages may correspond to different energy levels. The tube voltage of the radiation source 115 may be switched, and the energy level of the radiation beam emitted by the radiation source 115 may switch accordingly. The detector 112 may detect the radiation beam emitted from the radiation source 115. After the detector 112 receives the radiation beam passing through the subject, the received radiation beam may be converted into visible lights. The visible lights may be converted into electrical signals. The electrical signals may be further converted into digital information using an analog-to-digital (AD) converter. The digital information may be transmitted to a computing device (e.g., the processing device 140) for processing, or transmitted to a storage device (e.g., the storage device 150) for storage. In some embodiments, the detector 112 may include one or more detector units. The detector unit(s) may be and/or include single-row detector elements and/or multi-row detector elements. In some embodiments, the multi-energy CT device 110 may include a collimator (not shown) between the radiation source 115 and the subject. The collimator may be configured to control a shape and/or limit a width of the radiation beam emitted from the radiation source 115. The collimator may form an aperture through which the radiation beam may pass and form a radiation field. The larger the aperture of the collimator is, the larger the radiation field may be. The aperture size of the collimator may also be referred to as a collimator width.

For illustration purposes, a coordinate system 116 is provided in FIG. 1. The coordinate system 116 may be a Cartesian system including an X-axis, a Y-axis, and a Z-axis. The X-axis and the Z-axis as shown in FIG. 1 may be horizontal and the Z-axis may be vertical. As illustrated, the positive X direction along the X-axis may be from the left side to the right side of the table 114 viewed from the direction facing the front of the multi-energy CT device 110; the positive Z direction along the Z-axis shown in FIG. 1 may be from the end to the head of the table 114; the positive Y direction along the Y-axis shown in FIG. 1 may be from the lower part to the upper part of the multi-energy CT device 110.

In some embodiments, the multi-energy CT device 110 may scan the subject according to a slow kV-switching mode. That is, the scan of the subject may include a plurality of sub-scans (e.g., a first sub-scan, a second sub-scan, a third sub-scan, . . . ). Two consecutive sub-scans (e.g., the first sub-scan and the second sub-scan, or the second sub-scan and the third sub-scan, etc.) of the plurality of sub-scans may be at two different energy levels. For example, during the scan of the subject, the gantry 111 may rotate along a rotation axis parallel to the Z-axis, and the table 114 may move along a direction parallel to the Z-axis. The radiation source 115 and the detector 112 may rotate along with the gantry 111, and the subject may move along with the table 114. A rotation center of the radiation source 115 may also be referred to as an isocenter of the multi-energy CT device 110. The scan may include a plurality of sub-scans (e.g., a first sub-scan, a second sub-scan, a third sub-scan, . . . ).

Taking the multi-energy CT device 110 being a dual-energy CT device as an example, the subject may be scanned at two different energy levels. In the first sub-scan, the radiation source 115 may be applied with a tube voltage of a first kV (e.g., a relatively high kV such as 140 kV) to emit the radiation beam with a first energy level during which the gantry 111 rotates by a first angle. After the first sub-scan, the tube voltage of the radiation source 115 may be switched from the first kV to a second kV (e.g., a relatively low kV such as 80 kV), such that the first sub-scan may be switched to the second sub-scan. In the second sub-scan, the radiation source 115 may be applied with the tube voltage with the second kV during which the gantry 111 rotates by a second angle. The second angle may be the same as or different from the first angle. After the second sub-scan, the tube voltage of the radiation source 115 may be switched from the second kV to the first kV, such that the second sub-scan may be switched to the third sub-scan. During each sub-scan of the plurality of sub-scans, the detector 112 may detect the radiation beam emitted from the radiation source 115. There may be a switch time, the time that a switch between any two consecutive sub-scans of the plurality of sub-scans may take. During the switch, the radiation source 115 may emit no radiation beam and the detector 112 may detect no radiation beam. The larger a difference between the two energy levels of the two consecutive sub-scans is, the larger the switch time may be. Scan data acquired at the same energy level may be reconstructed to generate an image for subsequent processing.

The processing device 140 may process data and/or information. The data and/or information may be obtained from the multi-energy CT device 110, the terminal(s) 130, and/or the storage device 150. For example, the processing device 140 may obtain a parameter set associated with a scan to be performed using the multi-energy CT device 110. The processing device 140 may determine a maximum pitch associated with the scan based on a correlation relationship and the parameter set. As another example, the processing device 140 may cause the multi-energy CT device to perform a scan according to the maximum pitch and the parameter set. As still another example, the processing device 140 may reconstruct one or more images based on scan data acquired by the multi-energy CT device 110. In some embodiments, the processing device 140 may be a single server or a server group. The server group may be centralized or distributed. In some embodiments, the processing device 140 may be local or remote. For example, the processing device 140 may access information and/or data stored in the multi-energy CT device 110, the terminal (s)130, and/or the storage device 150 via the network 120. As another example, the processing device 140 may be directly connected to the multi-energy CT device 110, the terminal(s) 130, and/or the storage device 150 to access stored information and/or data. In some embodiments, the processing device 140 may be implemented on a cloud platform. For example, a cloud platform may include a private cloud, a public cloud, a hybrid cloud, a community cloud, a distributed cloud, an inter-cloud, and a multi-cloud, or the like, or any combination thereof. In some embodiments, the processing device 140 may be implemented by a computing device 200 having one or more components as illustrated in FIG. 2.

The terminal 130 may input/output signals, data, information, etc. In some embodiments, the terminal 130 may enable a user interaction with the processing device 140. For example, the terminal 130 may display an image of the subject on a screen. As another example, the terminal 130 may obtain a user's input information through an input device (e.g., a keyboard, a touch screen, a brain wave monitoring device), and transmit the input information to the processing device 140 for further processing. The terminal 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, a pair of glasses, a helmet, a watch, clothing, a backpack, a smart accessory, or the like, or any combination thereof. In some embodiments, the mobile device may include a mobile phone, a personal digital assistant (PDA), a navigation device, a point of sale (POS) device, a laptop computer, a tablet computer, a desktop computer, or the like, or any combination thereof. In some embodiments, the virtual reality device and/or augmented reality device may include a virtual reality helmet, a pair of virtual reality glasses, a virtual reality patch, an augmented reality helmet, a pair of augmented reality glasses, an augmented reality patch, or the like, or any combination thereof. For example, the virtual reality device and/or augmented reality device may include a Google Glass™, an Oculus Rift™, a HoloLens™, a Gear VR™, or the like. In some embodiments, the terminal 130 may be part of the processing device 140. In some embodiments, the terminal 130 may be integrated with the processing device 140 as an operation station of the multi-energy CT device 110. Merely by way of example, a user/operator (for example, a doctor) of the medical imaging system may control an operation of the multi-energy CT device 110 through the operation station.

In some embodiments, the terminal 130 may include an interface configured to facilitate an interaction between the user and the medical imaging system 100 (e.g., the processing device 140). For example, the interface may include a protocol selection area, a pitch determination icon (e.g., button), and a scan icon (e.g., button). The protocol selection area may be configured to receive a scan protocol selection instruction for selecting a target protocol from a plurality of scan protocols. Each of the plurality of scan protocols may include a parameter set including multiple scan parameters and multiple reconstruction parameters. The pitch determination icon may be configured to receive a maximum pitch determination instruction for determining a maximum pitch based on a target parameter set of the target scan protocol and a correlation relationship. The correlation relationship may describe a correlation between a pitch of the multi-energy CT device 110 and a parameter set of a scan protocol of the multi-energy CT device 110. The scan parameter set of a scan protocol may include one or more parameters including multiple scanning parameters and/or multiple reconstruction parameters. The correlation relationship may be determined according to a data sufficiency need. The scan icon may be configured to receive a scan instruction for causing the multi-energy CT device 110 to perform a target scan according to the target scan protocol and the maximum pitch. The scan icon may also be configured to determine whether the data sufficiency need is satisfied. In response to determining that the data sufficiency need is satisfied, the scan icon may be configured to direct the multi-energy CT device 100 to perform the scan; in response to determining that the data sufficiency need does not satisfied, the scan icon may be configured to adjusting one or more parameters of the parameter set and/or the pitch. More descriptions regarding the parameter set and the data sufficiency need may be found elsewhere in the present disclosure (e.g., FIGS. 5-7 and the descriptions thereof.

The storage device 150 may store data (e.g., scan data of a subject), instructions, and/or any other information. In some embodiments, the storage device 150 may store data obtained from the multi-energy CT device 110, the terminal(s) 130 and/or the processing device 140. For example, the storage device 150 may store scan data of a subject obtained from the multi-energy CT device 110. In some embodiments, the storage device 150 may store data and/or instructions executed or used by the processing device 140 to perform exemplary methods described in the present disclosure. In some embodiments, the storage device 150 may include a mass storage device, a removable storage device, a volatile read-write memory, a read-only memory (ROM), or the like, or any combination thereof. For example, the mass storage device may include a magnetic disk, an optical disk, a solid-state drive, a mobile storage device, etc. The removable storage device may include a flash drive, a floppy disk, an optical disk, a memory card, a ZIP disk, a magnetic tape, etc. The volatile read-and-write memory may include a random access memory (RAM). The RAM may include a dynamic RAM (DRAM), a double date rate synchronous dynamic RAM (DDR-SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 150 may be implemented by the cloud platform described in the present disclosure. For example, a cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components (e.g., the processing device 140, the terminal 130, etc.) of the medical imaging system. One or more components of the medical imaging system may access the data or instructions in the storage device 150 via the network 120. In some embodiments, the storage device 150 may be a part of the processing device 140 or may be independent and directly or indirectly connected to the processing device 140.

The network 120 may include any suitable network that can facilitate the exchange of information and/or data of the medical imaging system. In some embodiments, one or more components of the medical imaging system (e.g., the multi-energy CT device 110, the terminal 130, the processing device 140, the storage device 150, etc.) may communicate information and/or data with one or more components of the medical imaging system via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, server computers, or the like, or a combination thereof. For example, the network 120 may include a wireline network, an optical fiber network, a telecommunication network, a local area network, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 120 may include one or more network access points. For example, the network 120 may include wired and/or wireless network access points, such as base stations and/or Internet exchange points, through which one or more components of the medical imaging system may be connected to the network 120 to exchange data and/or information.

It should be noted that the above description regarding the medical imaging system is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical imaging system may include one or more additional components and/or one or more components of the medical imaging system described above may be omitted. In some embodiments, a component of the medical imaging system may be implemented on two or more sub-components. Two or more components of the medical imaging system may be integrated into a single component.

FIG. 2 is a schematic diagram illustrating exemplary hardware and/or software components of an exemplary computing device according to some embodiments of the present disclosure. The computing device 200 may be configured to implement any component of the medical imaging system. For example, the multi-energy CT device 110, the terminal 130, the processing device 140, and/or the storage device 150 may be implemented on the computing device 200. Although only one such computing device is shown for convenience, the computer functions relating to the medical imaging system as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program codes) and perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal 130 and/or the storage device 150. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the multi-energy CT device 110, the terminal 130, the storage device 150, or any other component of the medical imaging system. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 120) to facilitate data communications. The communication port 240 may establish connections between the processing device 140 and the multi-energy CT device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth™ network, a Wi-Fi network, a WiMax network, a WLAN, a ZigBee™ network, a mobile network (e.g., 3G, 4G, 5G), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
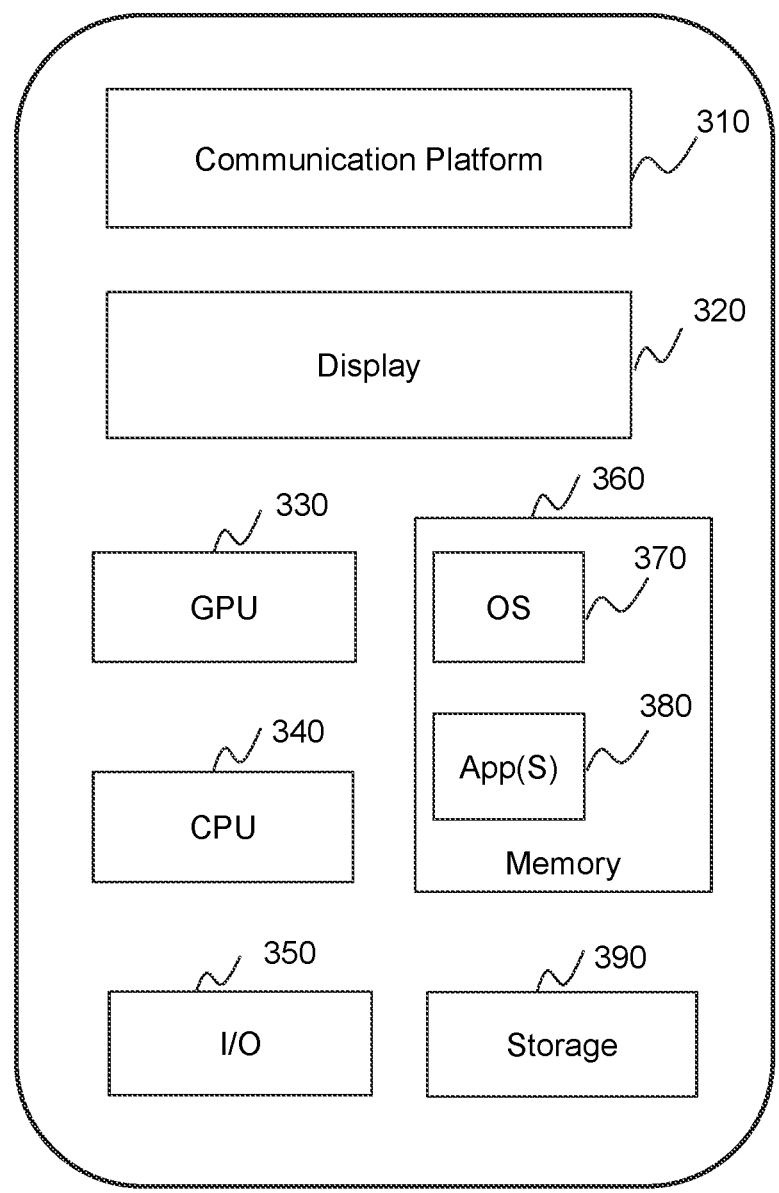
FIG. 3 is a schematic diagram illustrating hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the processing device 140 or the terminal 130 may be implemented on the mobile device 300.

As illustrated in FIG. 3, the mobile device 300 may include a communication module 310, a display 320, a graphics processing unit (GPU) 330, a central processing unit (CPU) 340, an I/O 350, a memory 360, and storage 390. The CPU 340 may include interface circuits and processing circuits similar to the processor 210. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to imaging from the mobile device 300. User interactions with the information stream may be achieved via the I/O devices 350 and provided to the processing device 140 and/or other components of the medical imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of workstation or terminal device. A computer may also act as a server if appropriately programmed.

Figure 4:
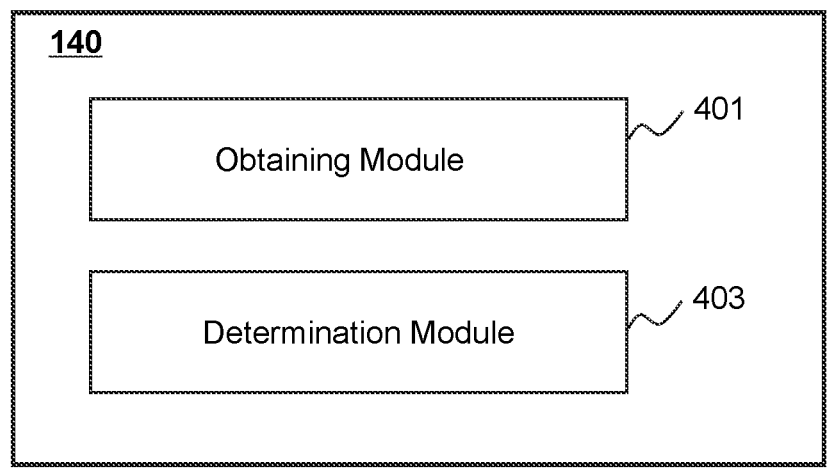
FIG. 4 a block diagram illustrating an exemplary processing device according to some embodiments of the present disclosure.

FIG. 4 is a schematic diagram illustrating an exemplary processing device according to some embodiments of the present disclosure. As shown in FIG. 4, the processing device 140 may include an obtaining module 401, and a determination module 403.

The obtaining module 401 may be configured to obtain data/information related to scanning and/or image reconstruction. For example, the obtaining module 401 may obtain a parameter set, or a portion thereof, associated with a scan to be performed using the multi-energy CT device 110 from one or more components (e.g., the storage device 150, the terminal device 130, etc.) of the medical imaging system 100 or an external storage device. The parameter set may include multiple scanning parameters and multiple reconstruction parameters. For instance, the obtaining module 401 may obtain related parameter(s) of a parameter (e.g., a switch time) of the parameter set and determine the parameter based on the related parameter(s). As another example, the obtaining module 401 may obtain a parameter correlation set or a portion thereof from the one or more components of the medical imaging system 100 or the external storage device. More descriptions regarding the obtaining of the parameter set and/or the parameter correlation set may be found elsewhere in the present disclosure (e.g., operation 501, FIG. 7, and operation 801 and the descriptions thereof).

The determination module 403 may be configured to determine a maximum pitch associated with the scan. For example, the determination module 403 may obtain (e.g., by determining or retrieving) a correlation relationship that describes a correlation between a pitch and the parameter set according to a data sufficiency need. The determination module 403 may determine the maximum pitch based on the correlation relationship and the parameter set. For instance, the correlation relationship may be in a form of a function of the parameter set. The determination module 403 may determine the maximum pitch by plugging the parameter set into the function of the parameter set. In some embodiments, the determination module 403 may determine a target pitch of the scan based on the maximum pitch. The target pitch may be less than or equal to the maximum pitch. In some embodiments, the determination module 403 may determine an adjusted parameter set by updating at least one parameter of the parameter set. More descriptions regarding the determination of the maximum pitch, the target pitch, and/or the adjusted parameter set elsewhere in the present disclosure (e.g., operations 503, 803, and 805 and the descriptions thereof).

The modules in the processing device 140 may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth™, a ZigBee™, a Near Field Communication (NFC), or the like, or any combination thereof. Each of the modules described above may be a hardware circuit that is designed to perform certain actions, e.g., according to a set of instructions stored in one or more storage media, and/or any combination of the hardware circuit and the one or more storage media. In some embodiments, the processing device 140 may include one or more other modules and/or one or more modules described above may be omitted. For example, the processing device 140 may include a scanning module for causing the multi-energy CT device 110 to perform the scan. As another example, the processing device 140 may include a storage module (not shown) configured to store information and/or data (e.g., the maximum pitch, the correlation relationship, scan data, images) associated with the above-mentioned modules. As still another example, the processing device 140 may include a reconstruction module configured to generate one or more images based on the scan data acquired during the scan. Additionally or alternatively, two or more modules may be integrated into a single module, and/or a module may be divided into two or more units. For example, the above-mentioned modules may be integrated into a console (not shown). Via the console, a user may set and/or adjust one or more parameters of the parameter set and/or the pitch for scanning a subject, controlling imaging processes, setting or adjusting parameters for the reconstruction of an image, viewing images, etc. As another example, the determination module 403 may be divided into multiple units including, e.g., a unit for determining the maximum pitch, a unit for determining a target pitch, and a unit for determining an adjusted parameter set.

FIG. 5 is a flowchart illustrating an exemplary process for determining a maximum pitch according to some embodiments of the present disclosure. In some embodiments, process 500 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In some embodiments, before a scan is performed using a multi-energy CT device (e.g., the multi-energy CT device 110), a plurality of parameters may need to be determined for the scanning and/or image reconstruction. Among the plurality of parameters, a pitch of the multi-energy CT device may be used to measure the moving speed of the table 114 during the scan to be performed. The pitch refers to a ratio of a distance that the table 114 moves when the gantry 111 rotates a circle (i.e., 360 degrees) to the collimation width. If the pitch is excessively small, the scan speed of the scan (e.g., the moving speed of the table during the scan) may be too low to satisfy a target scan speed. If the pitch is excessively large, the data sufficiency need may not be satisfied. Accordingly, before the scan, the pitch may need to be determined according to a specific condition of a subject (e.g., a patient) to be scanned using the multi-energy CT device, such that not only the target scan speed but also the data sufficiency need may be achieved.

In 501, the processing device 140 (e.g., the obtaining module 401) may obtain a parameter set associated with a scan to be performed by a multi-energy CT device (e.g., the multi-energy CT device 110).

In some embodiments, the scan to be performed by the multi-energy CT device 110 may include a scan to be performed on the subject by the multi-energy CT device 110. The subject may include a biological subject or a non-biological subject. The biological subject may be a human being, an animal, or a specific portion thereof (e.g., an organ and/or tissue thereof). For example, the subject may include a patient, or a portion thereof. The non-biological subject may include a phantom of a human being, an animal, or a portion thereof.

In some embodiments, the scan may be performed using the multi-energy CT device 110 according to a slow kV-switching mode as described in FIG. 1. The scan may include a plurality of sub-scans. At least a portion of the plurality of sub-scans may be performed at different energy levels alternately. For instance, each of two consecutive sub-scans of at least a portion of the plurality of sub-scans may alternate between two different energy levels. For example, a first sub-scan of the two consecutive sub-scans may be performed at a first energy level (e.g., a relatively high energy level), and a second sub-scan of the two consecutive sub-scans may be performed at a second energy level (e.g., a relatively low energy level). Two sub-scans of the plurality of sub-scans that are performed at the same energy level and closest to each other in sequence (i.e., between the two sub-scans there is no other sub-scan performed at the same energy level) may also be referred to as two consecutive sub-scans with the same energy level. For the multi-energy CT device 110 being a dual-energy CT device, every other sub-scan of at least a portion of the plurality of sub-scans may constitute two consecutive sub-scans with the same energy level.

As described in connection with FIG. 1, the multi-energy CT device 110 may include the gantry 111, the collimator (not shown), the radiation source 115, and the isocenter (i.e., the rotation center of the radiation source 115). In some embodiments, the parameter set may include multiple scanning parameters that may be used for performing the scan and multiple reconstruction parameters that may be used for image reconstruction based on scan data acquired in the scan.

The multiple scanning parameters may include a rotation velocity of the gantry 111 (or a rotation velocity of the radiation source 115), a collimation width (i.e., an aperture size) of the collimator, a current time product of a sub-scan at an energy level, a switch time between the two consecutive sub-scans, a scan angle of a sub-scan at the energy level, a distance between the radiation source and the isocenter (SID), or the like, or any combination thereof. The current time product of the sub-scan at an energy level refers to a product of a tube current corresponding to the energy level and an exposure time during the sub-scan (e.g., a duration of the sub-scan). For the dual-energy CT device, the current time product may include a first current time product corresponding to the first energy level and a second current time product corresponding to the second energy level. The switch time between the two consecutive sub-scans refers to a time interval when the tube voltage of the radiation tube switches from the first kV to the second kV or from the second kV to the first kV. The scan angle of a sub-scan at an energy level refers to a rotation angle (e.g., 240 degrees) of the gantry 111 (or the radiation source 115) during the sub-scan at the energy level.

In some embodiments, the scan angle of a sub-scan may span a continuous range. Scan angles of different sub-scans at a same energy level may be the same or different. For example, scan angles of different sub-scans at the first energy level may be the same, and scan angles of different sub-scans at the second energy level may be the same. Accordingly, the scan angle may include a first scan angle of a sub-scan at the first energy level and a second scan angle of a sub-scan at the second energy level. In some embodiments, scan angles of sub-scans at different energy levels may be the same or different. For example, a scan angle range of a sub-scan (e.g., the first sub-scan) at the first energy level may be the same as a scan angle range of a sub-scan (e.g., the second sub-scan) at the second energy level.

The multiple reconstruction parameters may include a reconstruction field of view (FOV), a reconstruction range (defined by, e.g., a length and a width, a diameter, etc.) of the reconstruction FOV, a reconstruction center, a reconstruction image thickness (e.g., 5 mm), and a reconstruction angle of a sub-scan at an energy level. Among the scan data acquired during the sub-scan, a portion may be selected for reconstruction by setting or adjusting the reconstruction angle. The reconstruction angle of a sub-scan at an energy level may be equal to the scan angle of the sub-scan at the energy level or a portion of the scan angle of the sub-scan at the energy level.

In some embodiments, the parameter set may be pre-stored in a storage device (e.g., the storage device 150, the storage device 220, or the storage 390) of the medical imaging system 100 or an external storage device that is accessible by the medical imaging system 100, or a portion thereof (e.g., the processing device 140). The processing device 140 may retrieve the parameter set from the storage device or the external storage device. For example, the parameter set may be stored as a scanning protocol. There may be multiple scanning protocols stored in the storage device. The processing device 140 may obtain the parameter set from a corresponding scanning protocol including the parameter set, e.g., according to a user instruction. Alternatively, the processing device 140 may obtain a portion of the parameters of the parameter set from the storage device or the external storage device. The processing device 140 may determine the remaining parameters of the parameter set based on the portion of the parameters of the parameter set. For example, the processing device 140 may obtain the reconstruction center and the reconstruction range of the reconstruction FOV according to a user instruction (e.g., a user input). The processing device 140 may determine the reconstruction FOV based on the reconstruction center and the reconstruction range. As another example, the processing device 140 may obtain the first current time product of the first sub-scan according to a user instruction (e.g., a user input). The processing device 140 may determine the second current time product of the second sub-scan based on the first current product of the first sub-scan for further determining the switch time between the two consecutive sub-scans (e.g., between the first sub-scan and the second sub-scan), more description of which may be found in elsewhere in the present disclosure (e.g., FIG. 7 and the description thereof).

In 503, the processing device 140 (e.g., the determination module 403) may determine a maximum pitch based on a correlation relationship and the parameter set.

As used herein, the correlation relationship refers to a relationship that describes a correlation between the pitch of the multi-energy CT device 110 and the parameter set of a scan (e.g., a sub-scan). For example, the correlation relationship may include that the pitch negatively correlates with the reconstruction FOV, the pitch negatively correlates with the reconstruction image thickness, the pitch negatively correlates with the reconstruction angle range of a sub-scan at an energy level, the pitch positively correlates with the collimation width, the pitch negatively correlates with the continuous scan angle range of a sub-scan at the energy level, the pitch positively correlates with the SID, the pitch negatively correlates with the rotation velocity, the pitch negatively correlates with the switch time associated with the two consecutive sub-scans, or the like, or any combination thereof.

In some embodiments, the correlation relationship may be in the form of (or be represented by) a function of the parameter set (e.g., a function for determining at least a portion of the multiple scanning parameters and the reconstruction parameters based on at least another portion of the multiple scanning parameters and the reconstruction parameters of a same scan or sub-scan). For example, the function of the parameter set may be represented as $f(A)$, where A refers to the parameter set), and the correlation relationship may be represented as a pitch equal to or less than ($\leq$)$f(A)$. The processing device 140 may determine the maximum pitch by plugging the parameter set A into the function of the parameter set $f(A)$.

In some embodiments, the correlation relationship may be pre-stored in a storage device as described elsewhere in the present disclosure. The processing device 140 may retrieve the correlation relationship from the storage device. Alternatively, the processing device 140 may determine the correlation relationship based on the data sufficiency need. During the scan, there may be an interval between two consecutive sub-scans (e.g., a first sub-scan and a third sub-scan) with the same energy level. During the first sub-scan, the table 114 may move from a first position to a second position. During the third sub-scan, the table 114 may move from a third position to a fourth position. During the period when the table 114 moves from the second position to the third position, the first sub-scan may be switched to the second sub-scan, the second sub-scan may be performed, and the second sub-scan may be switched to the third sub-scan; that is, during the period, the energy levels switch twice which take two switch times and the second sub-scan occurs once. As used herein, the interval between two consecutive sub-scans with the same energy level refers to a first distance (denoted as L) from a first center between the first position and the second position and a second center between the third position and the fourth position. As scan data of sub-scans with the same energy level may be used to generate a target image of the subject by way of image reconstruction, the interval between two consecutive sub-scans with the same energy level may need to be less than or equal to a second distance (denoted by S) for satisfying the data sufficiency need. That is, the data sufficiency need may be satisfied by specifying that the first distance is less than or equal to the second distance (i.e., L≤S). The second distance may be the maximum value of the first distance. That is, the second distance refers to a maximum interval between the two consecutive sub-scans with the same energy level. The processing device 140 may determine the correlation relationship based on the data sufficiency need; i.e., the processing device 140 may determine "the pitch≤$f(A)$" based on "L≤S."

Figure 6A:
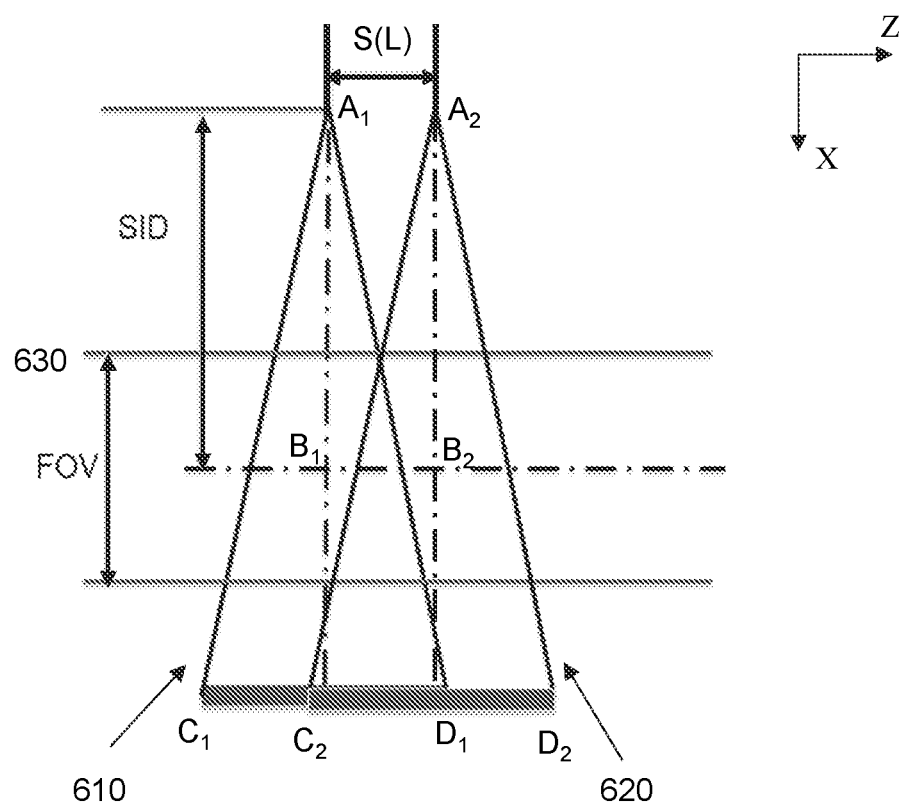
FIGS. 6A-6C are schematic diagrams illustrating exemplary two consecutive sub-scans with a same energy level according to some embodiments of the present disclosure.
Figure 6B:
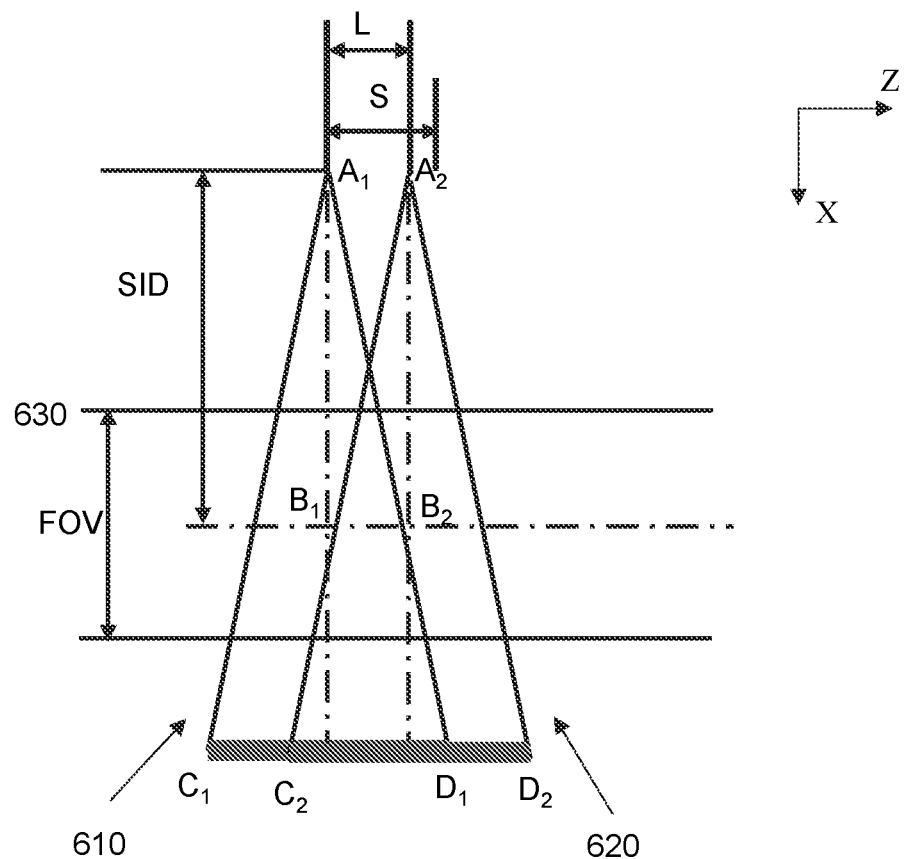
Figure 6C:
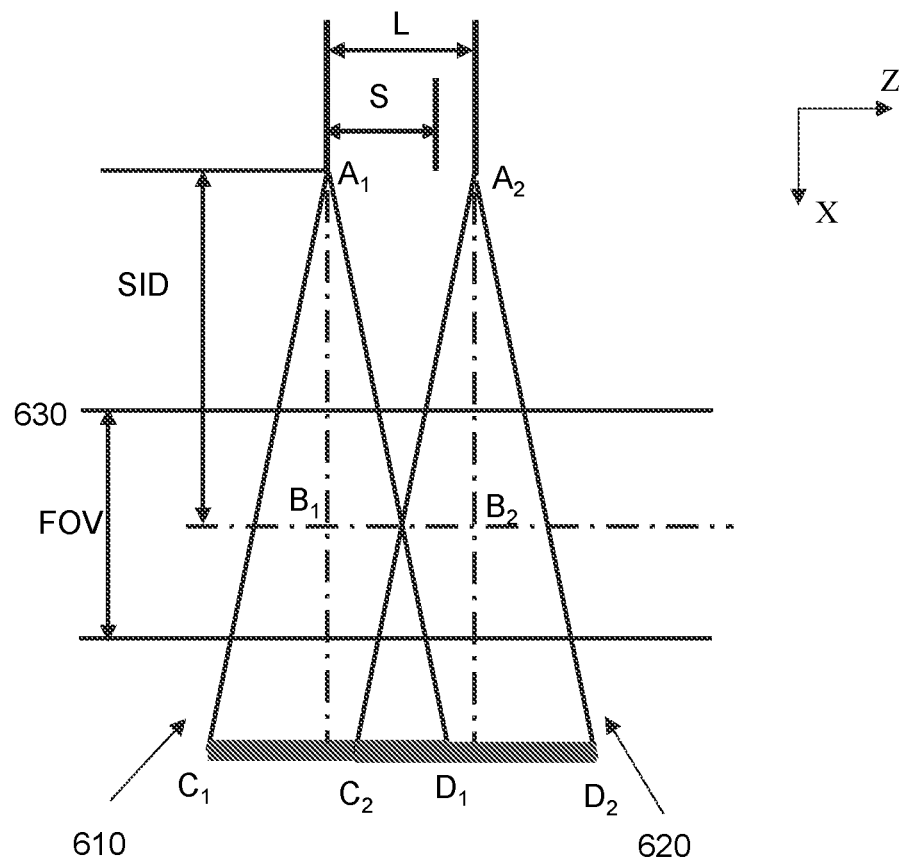

FIGS. 6A-6C are schematic diagrams illustrating exemplary two consecutive sub-scans (e.g., the first sub-scan and the third sub-scan) at the same energy level of the multi-energy CT device 110 according to some embodiments of the present disclosure. FIGS. 6A-6C are a top view of the X-Z plane, where the X and Z axes are the same as those illustrated in FIG. 1. As shown in FIG. 6A, SID denotes a distance between the radiation source 115 (denoted as $A_i$ (e.g., $A_1$, $A_2$) in FIG. 6A) to the rotation center or isocenter (denoted by $B_i$ (e.g., $B_1$, $B_2$) in FIG. 6A) of the radiation source 115. FOV denotes a reconstruction FOV (e.g., a range of the view shown in a reconstruction image). A triangle 610 ($A_1C_1D_1$) denotes a radiation range of the first sub-scan along the Z-axis. A triangle 620 ($A_2C_2D_2$) denotes a radiation range of the third sub-scan along the Z-axis. L denotes the first distance, the interval between the first sub-scan and the third sub-scan along the Z-axis, the two consecutive sub-scans with the same energy level. S as illustrated in FIG. 6A denotes the second distance when the intersection of the edge $A_1D_1$ of the triangle 610 and the edge $A_2C_2$ of the triangle 620 (substantially) coincide with an edge 630 of FOV, such that the data sufficiency need is satisfied.

FIG. 6A illustrates an ideal condition that L is equal to S to satisfy the data sufficiency need. In some embodiments, L may be (slightly) less than S to ensure satisfying the data sufficiency need. For example, L may be less than S by a preset distance to avoid the subject being subject to unnecessary radiation. As shown in FIG. 6B, the intersection of the edge $A_1D_1$ of the triangle 610 and the edge $A_2C_2$ of the triangle 620 does not (substantially) coincide with the edge 630 of FOV and is outside the FOV, ensuring that image data so acquired is sufficient. In some embodiments, if L is greater than S as shown in FIG. 6C, the intersection of the edge $A_1D_1$ of the triangle 610 and the edge $A_2C_2$ of the triangle 620 does not (substantially) coincide with the edge 630 of FOV and is within FOV, indicating that a portion of the subject is not irradiated and therefore its information (e.g., anatomical information) may be insufficiently reflected in the image data so acquired and the data sufficiency need is not satisfied, which in turn may result in artifacts in a reconstructed image determined based on the image data so acquired.

In some embodiments, the first distance may correlate with a first plurality of parameters of the parameter set. The first plurality of parameters may include the scan angle of a sub-scan at the energy level, the pitch, the collimation width of the collimator, the rotation velocity of the gantry 111 (or the rotation velocity of the radiation source 115), the switch time between the two consecutive sub-scans, a reconstruction angle of a sub-scan at the energy level, or the like, or any combination thereof. The processing device 140 may obtain (e.g., by way of determining or retrieving) a first function for determining the first distance. The first function for determining the first distance may be denoted as $L=L(x_1, x_2, x_3, \cdots, x_n)$, where $x_1, x_2, x_3, \cdots, x_n$ denote the first plurality of parameters. For example, the first function for determining the first distance may indicate that the first distance positively correlates with the reconstruction angle range of a sub-scan at an energy level, the first distance positively correlates with the collimation width, the first distance positively correlates with the continuous scan angle range of a sub-scan at the energy level, the first distance positively correlates with the rotation velocity, the first distance positively correlates with the switch time associated with the two consecutive sub-scans, the first distance positively correlates with the pitch, or the like, or any combination thereof.

In some embodiments, the second distance may correlate with a second plurality of parameters of the parameter set. The second plurality of parameters may be different from the first plurality of parameters, e.g., partially overlapping with the first plurality of parameters. The second plurality of parameters may include the reconstruction FOV, the reconstruction image thickness, the SID, the collimation width, or the like, or any combination thereof. The processing device 140 may obtain (e.g., by way of determining or retrieving) a second function for determining the second distance. The second function for determining the second distance may be denoted as $S=L(x'_1, x'_2, x'_3, \ldots, x'_m)$, where $x'_1, x'_2, x'_3, \ldots, x'_m$ denote the second plurality of parameters. The second function for determining the second distance may indicate that the second distance negatively correlates with the reconstruction FOV, the second distance positively correlates with the SID, the second distance positively correlates with the collimation width, and the second distance negatively correlates with the reconstruction image thickness, or the like, or any combination thereof. Merely by way of example, the second function for determining the second distance may be in the form of $S=(1-FOV/2/SID)*$collimation width.

Further, the processing device 140 may determine the correlation relationship (i.e., a relationship between the pitch and the parameter set) based on $L \leq S$, the first function for determining the first distance, and the second function for determining the second distance. Accordingly, the processing device 140 may determine the maximum pitch based on the correlation relationship.

In some embodiments, the processing device 140 may determine the maximum pitch as a target pitch. Alternatively, the processing device 140 may determine the target pitch based on the maximum pitch and the target scan speed. The target pitch may be less than or equal to the maximum pitch.

Further, the processing device 140 may cause the multi-energy CT device 110 to perform the scan according to the target pitch and the parameter set, which can satisfy not only the data sufficiency need but also the target scan speed, and accordingly, medical image(s) reconstructed based on scan data acquired during the scan may meet a preset standard (e.g., clinical need). In some embodiments, the processing device 140 may adjust at least one parameter of the parameter set based on the target pitch and the correlation relationship (e.g., adjusting, based on the correlation relationship, at least one parameter of the parameter set according to the target pitch). For example, the processing device 140 may determine a correlation between the at least one parameter and the pitch based on the correlation relationship. The processing device 140 may adjust the at least one parameter based on the determined correlation and the target pitch. As another example, the processing device 140 may adjust the at least one parameter until an updated first distance (L') and an updated second distance (S') (that are determined based on the target pitch and the adjusted parameter set) satisfy $L' \leq S'$. In some embodiments, the processing device 140 may determine, among the parameter set, one or more parameters that have a minimal impact on the imaging effect as the at least one parameter for adjustment, thereby simplifying the adjustment. Further, the processing device 140 may cause the multi-energy CT device 110 to perform the scan according to the adjusted parameter set and the target pitch.

According to some embodiments of the present disclosure, the parameters (e.g., the pitch of the multi-energy CT device 110, and/or the parameter set) associated with the scan may be determined and adjusted automatically, which may improve the efficiency and accuracy of the scan.

In some embodiments, the processing device 140 may determine other correlation relationships each of which may indicate a correlation between a specific parameter (except the pitch) of the parameter set and the remaining parameters of the parameter set and the pitch, which is similar to the determination of the correlation relationship that describes the correlation between the pitch and the parameter set. Further, the processing device 140 may determine and/or adjust the specific parameter based on a corresponding correlation relationship, the pitch, and the remaining parameters.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more additional operations may be added in the process 500. For example, a storing operation may be added elsewhere in the process 500. In the storing operation, the processing device 140 may store information and/or data used or obtained (e.g., the maximum pitch, the correlation relationship, etc.) in operations of the process 500 in a storage device (e.g., the storage device 150) disclosed elsewhere in the present disclosure. As another example, an additional operation may be added after operation 503 for causing the multi-energy CT device 110 to perform the scan. As still another example, an additional operation may be added elsewhere in the process 500 for determining the target pitch and/or adjusting the parameter set.

Figure 7:
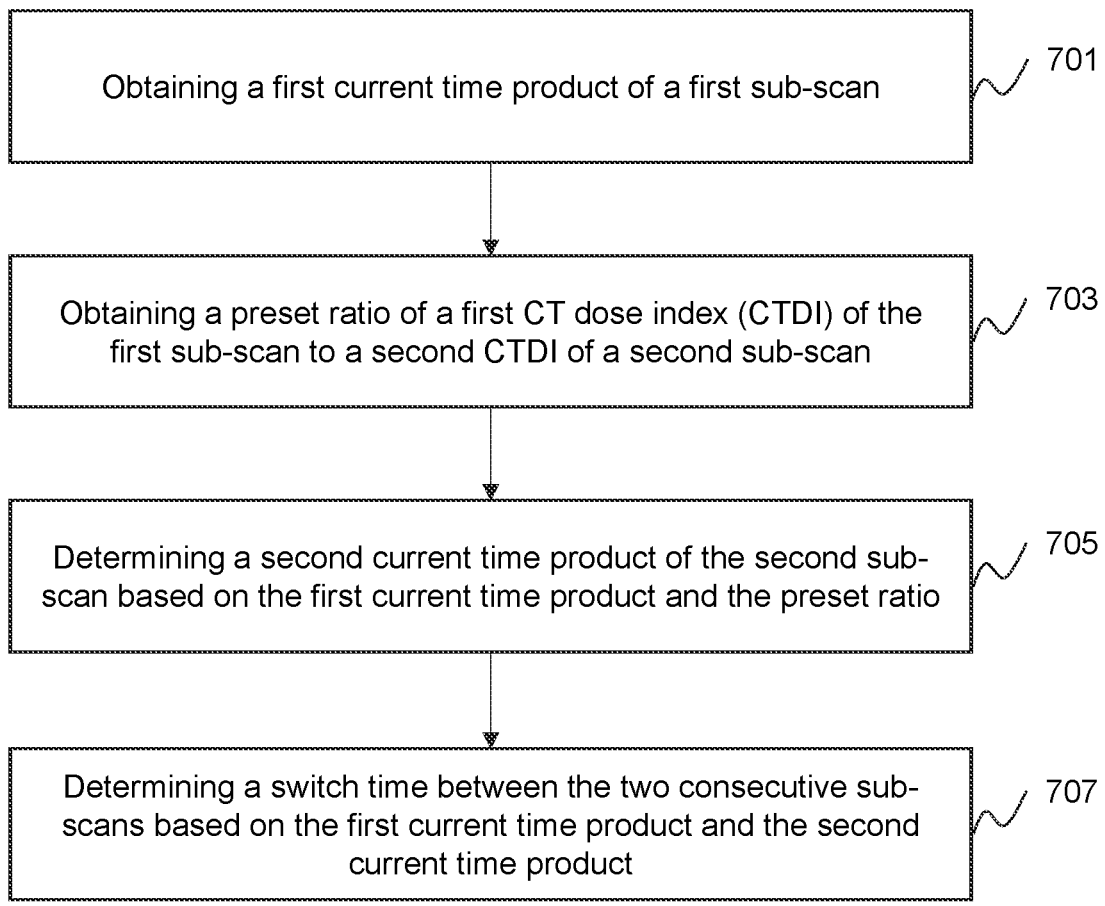
FIG. 7 is a flowchart illustrating an exemplary process for determining a switch time between two consecutive sub-scans according to some embodiments of the present disclosure.

FIG. 7 is a flowchart illustrating an exemplary process for determining a switch time between two consecutive sub-scans according to some embodiments of the present disclosure. In some embodiments, process 700 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, at least part of operation 501 in FIG. 5 may be achieved by the process 700.

As described in FIG. 5, the two consecutive sub-scans may include the first sub-scan at the first energy level (e.g., a relatively high energy level) and the second sub-scan at the second energy level (e.g., a relatively low energy level). During the first sub-scan, the radiation source 115 may be applied with a first tube voltage. During the second sub-scan, the radiation source 115 may be applied with a second tube voltage.

In 701, the processing device 140 (e.g., the obtaining module 401) may obtain a first current time product of the first sub-scan.

The processing device 140 may obtain the first current time product according to a user instruction (e.g., a user input via an interface of the medical imaging system 100). Alternatively, the processing device 140 may obtain the first current time product from a storage device as described elsewhere in the present disclosure.

In 703, the processing device 140 (e.g., the obtaining module 401) may obtain a preset ratio of a first CT dose index (CTDI) of the first sub-scan to a second CTDI of the second sub-scan.

As used herein, a CTDI may represent a dose that a subject receives during a scan. The first CTDI may represent a radiation dose that the subject receives during the first sub-scan. The second CTDI may represent a radiation dose that the subject receives during the second sub-scan. In some embodiments, the preset ratio of the first CTDI to the second CTDI may be a default setting of the medical imaging system 100 or adjustable according to different situations. For example, images generated based on scan data acquired at different energy levels may need to have the same or similar image quality (e.g., same or similar noise) for further processing (e.g., for image registration). The preset ratio may be determined based on a constraint regarding the image quality and/a clinical requirement. As another example, the preset ratio may be a constant value.

In 705, the processing device 140 (e.g., the obtaining module 401) may determine a second current time product of the second sub-scan based on the first current time product and the preset ratio.

In some embodiments, the first CTDI may correlate with the first current time. The second CTDI may correlate with a second current time of the second sub-scan. For example, the first CTDI may positively correlate with the first current time product. The second CTDI may positively correlate with the second current time product. The processing device 140 may determine the second current time product of the second sub-scan based on one or more of the correlations described herein. In some embodiments, a ratio of the first current time product to the second current time product may be equal to the preset ratio. For example, if the preset ratio is 1, the first current time product may be equal to the second current time product. The processing device 140 may determine the second current time product based on the first current time product and the ratio.

In some embodiments, the ratio of the first current time product to the second current time product may be different from the preset ratio and have a relationship with the preset ratio. The processing device 140 may determine the ratio based on the preset ratio and the relationship. Merely by way of example, the relationship between the ratio and the preset ratio may be denoted as follows:

$$\frac{mAs_1}{mAs_2} \cong \frac{CTDI_1}{CTDI_2} * \frac{TableCoeff_2}{TableCoeff_1},$$

where $$\frac{mAs_1}{mAs_2}$$

denotes the ratio, $$\frac{CTDI_1}{CTDI_2}$$

denotes the preset ratio, $mAs_1$ denotes the first current time product, $mAs_2$ denotes the second current time product, $CTDI_1$ denotes the first CTDI, $CTDI_2$ denotes the second CTDI, $TableCoeff_1$ denotes a first coefficient factor under the first tube voltage, and $TableCoeff_2$ denotes a second coefficient factor under the second tube voltage. As used herein, a coefficient factor under a tube voltage (e.g., the first coefficient factor under the first tube voltage, the second coefficient factor under the second tube voltage) refers to a factor for correcting the tube voltage. The first coefficient factor refers to a factor for correcting the first tube voltage. The second coefficient factor refers to a factor for correcting the second tube voltage. Different scan conditions (e.g., different tube voltages) may correspond to different coefficient factors. The user may preset a coefficient correction table including the different coefficient factors corresponding to different scan conditions for adaptively adjusting the coefficient factor(s). The processing device 140 may retrieve the first coefficient factor and the second coefficient factor from the coefficient correction table, e.g., according to the first tube voltage and the second tube voltage. Further, the processing device 140 may determine the second current time product based on the first current time product, the first CTDI, the second CTDI, the first coefficient factor, and the second coefficient factor.

In 707, the processing device 140 (e.g., the obtaining module 401) may determine a switch time between the two consecutive sub-scans based on the first current time product and the second current time product.

In some embodiments, the processing device 140 may determine the switch time based on the first current time product and the second current time product according to a rule of the medical imaging system 100. The rule may specify that the switch time may positively correlate with a difference between the first current time product and the second current time product, positively correlate with a performance of the multi-energy CT device 110 (e.g., a performance of the radiation tube of the radiation source 115, a performance of a tube voltage generator), etc. The larger the difference between the first current time product and the second current time product is, the greater the switch time between the two consecutive sub-scans may be.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted in the process 700. For example, a storing operation may be added elsewhere in the process 700. In the storing operation, the processing device 140 may store information and/or data (e.g., the preset ratio) used or obtained in operations of the process 700 in a storage device (e.g., the storage device 150) disclosed elsewhere in the present disclosure. As another example, operations 703 and 705 may be omitted, and the processing device 140 may obtain the second current time product according to a user instruction.

Figure 8:
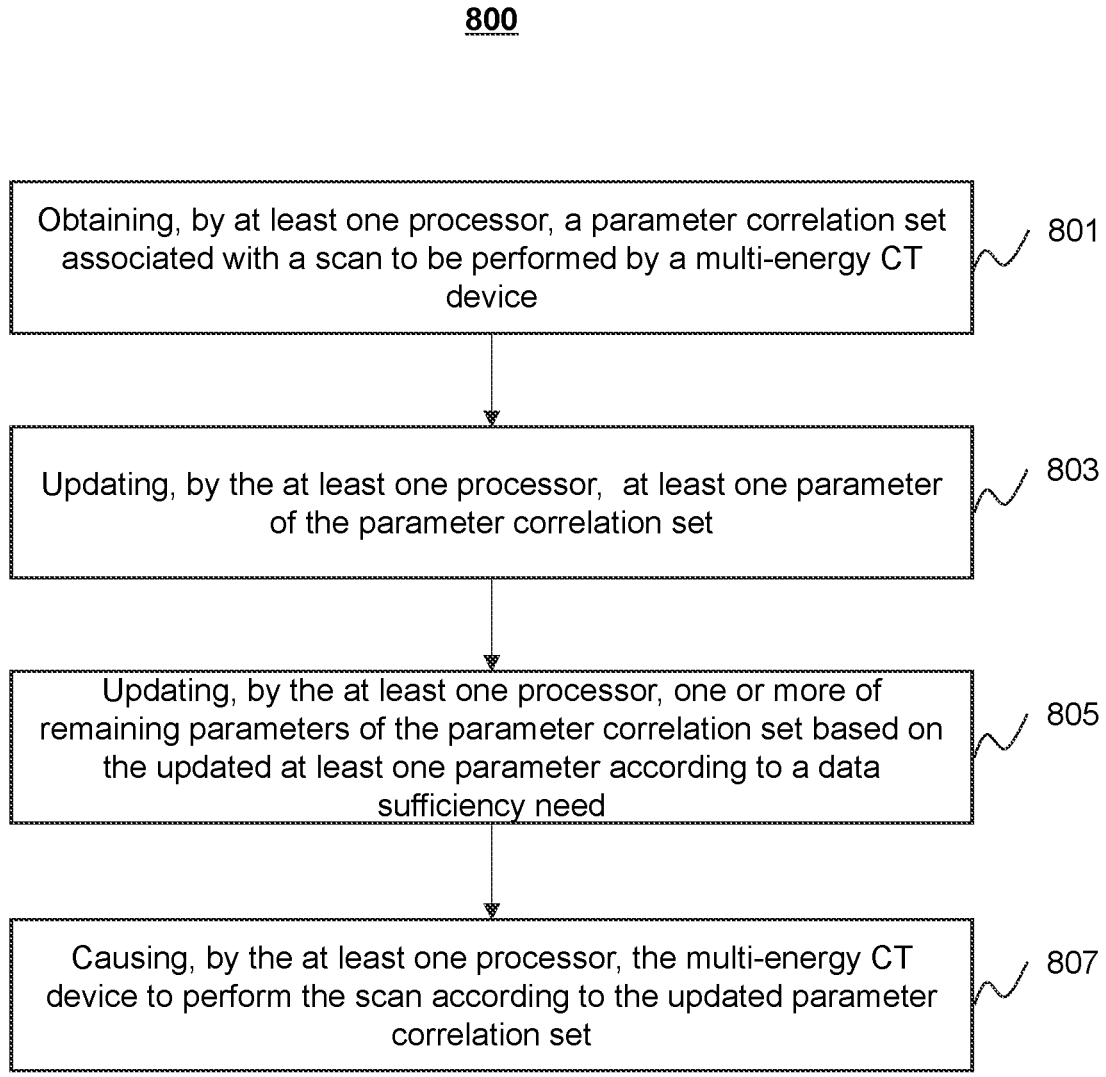
FIG. 8 is a flowchart illustrating an exemplary process for a parameter adjustment of a multi-energy CT device according to some embodiments of the present disclosure.

FIG. 8 is a flowchart illustrating an exemplary process for a parameter adjustment of a multi-energy CT device according to some embodiments of the present disclosure. In some embodiments, process 800 may be implemented as a set of instructions (e.g., an application) stored in a storage device (e.g., the storage device 150, the storage device 220, and/or the storage 390). The processing device 140 (e.g., the processor 210, the CPU 340, and/or one or more modules illustrated in FIG. 4) may execute the set of instructions, and when executing the instructions, the processing device 140 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

In 801, the processing device 140 may obtain a parameter correlation set associated with a scan to be performed by the multi-energy CT device 110. For example, the processing device 140 may determine the parameter correlation set based on a parameter set and a pitch of the multi-energy CT device 110. The parameter set may include multiple scanning parameters and multiple reconstructions parameters as described in operation 501 in FIG. 5. Accordingly, the parameter correlation set may include the multiple scanning parameters, the multiple reconstruction parameters, and the pitch. It should be noted that the pitch may also be referred to as a type of scanning parameter. In such cases, the parameter correlation set may also be referred to as including multiple scanning parameters (including the pitch) and multiple reconstruction parameters.

In some embodiments, the multiple scanning parameters and/or the multiple reconstruction parameters may be preset in different scanning protocols. Before the scan is performed by the multi-energy CT device 110, a target scanning protocol may be selected from the different scanning protocols to obtain the multiple scanning parameters and/or the multiple reconstruction parameters. For example, the processing device 140 may receive a user instruction associated with the target scanning protocol (e.g., a scan protocol selection instruction) via, e.g., an interface of the terminal device 130 as described in FIG. 1). The processing device 140 may select the target scanning protocol from the different scanning protocols according to the user instruction.

In 803, the processing device 140 may update at least one parameter of the parameter correlation set. In some embodiments, the processing device 140 may update the at least one parameter according to a user instruction.

In 805, the processing device 140 may update one or more of the remaining parameters of the parameter correlation set based on the updated at least one parameter.

In some embodiments, the processing device 140 may update the one or more of the remaining parameters (e.g., the pitch) according to the data sufficiency need and/or the target scanning speed. For example, the processing device 140 may determine the first distance and the second distance based on the updated at least one parameter and the remaining parameters of the parameter correlation set. In response to determining that the first distance is greater than the second distance, the processing device 140 may adjust one or more of the remaining parameters of the parameter correlation set until the updated first distance is less than or equal to the updated second distance and the target scanning speed is satisfied. For example, if the reconstruction FOV is updated in operation 803, the processing device 140 may update the pitch among the remaining parameters. As another example, if the pitch is updated in operation 803, the processing device 140 may update the reconstruction FOV and the rotation velocity of the gantry 111 (or the rotation velocity of the radiation source 115). It should be noted that the one or more of the remaining parameters to be updated may be determined according to different situations, which is not limiting, as long as the updated first distance is less than or equal to the updated second distance and the target scanning speed is satisfied.

In some embodiments, the processing device 140 may update the pitch based on the updated at least one parameter and other remaining parameters, e.g., according to the correlation relationship as described in operation 503 in FIG. 5. Since the correlation relationship is determined according to the data efficiency need, as long as the correlation relationship is satisfied, the data sufficiency need may be satisfied accordingly.

In 807, the processing device 140 may cause the multi-energy CT device 110 to perform the scan according to the updated parameter correlation set.

In some embodiments, the data sufficiency need (i.e., L≤S) may be a precondition of the scan. That is, in response to determining that the data sufficiency need is satisfied, the processing device 140 may direct the multi-energy CT device 100 to perform the scan; in response to determining that the data sufficiency need does not satisfied, the processing device 140 may proceed to adjust/update one or more parameters of the correlation parameter set (e.g., according to operations 801-805).

According to operations 801 to 807, when at least one parameter of the parameter correlation set is updated, the remaining parameter(s) of the parameter correlation set may be updated automatically, thereby reducing the workload of the user and improving the efficiency and accuracy of parameter adjustment. Thereafter, the processing device 140 may obtain scan data that satisfies the target scan speed and the data sufficiency need. Further, the processing device 140 may perform a reconstruction operation on the scan data to generate medical images that meet the clinical standard.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
at least one storage device including a set of instructions; and
at least one processor configured to communicate with the at least one storage device, wherein when executing the set of instructions, the at least one processor is configured to direct the system to perform operations including:

obtaining, by the at least one processor, a parameter set associated with a scan to be performed using a multi-energy computed tomography (CT) device, the parameter set including multiple scanning parameters and multiple reconstruction parameters; and determining, by the at least one processor, a maximum pitch associated with the scan based on a correlation relationship and the parameter set, wherein the correlation relationship describes a correlation between a pitch of the multi-energy CT device and the parameter set.

2. The system of claim 1, wherein
the multi-energy CT device includes a gantry, a collimator, a radiation source, and an isocenter;
the scan to be performed includes a plurality of sub-scans, at least two consecutive sub-scans of the plurality of sub-scans being at different energy levels; and
the multiple scanning parameters include a rotation velocity of the gantry, a collimation width of the collimator, a current time product of a sub-scan at an energy level, a switch time between the two consecutive sub-scans, a scan angle of a sub-scan at the energy level, and a distance between the radiation source and the isocenter (SID).

3. The system of claim 2, wherein
the multiple reconstruction parameters include a reconstruction field of view (FOV), a reconstruction range of the reconstruction FOV, a reconstruction center, a reconstruction image thickness, and a reconstruction angle of a sub-scan at the energy level.

4. The system of claim 3, wherein the correlation relationship includes at least one of the following:
the pitch negatively correlates with the reconstruction FOV;
the pitch s negatively correlates with the reconstruction image thickness;
the pitch negatively correlates with the reconstruction angle of a sub-scan at an energy level;
the pitch positively correlates with the collimation width;
the pitch negatively correlates with the scan angle of a sub-scan at the energy level;
the pitch positively correlates with the SID;
the pitch negatively correlates with the rotation velocity; or
the pitch negatively correlates with the switch time associated with the two consecutive sub-scans.

5. The system of claim 1, wherein the scan to be performed include a plurality of sub-scans, two consecutive sub-scans of the plurality of sub-scans include a first sub-scan and a second sub-scan, and the operations further include:
obtaining a first current time product of the first sub-scan;
obtaining a preset ratio of a first CT dose index (CTDI) of the first sub-scan to a second CTDI of the second sub-scan; and
determining a second current time product of the second sub-scan based on the first current time product and the preset ratio.

6. The system of claim 4, wherein
the first CTDI positively correlates with the first current time product, and
the second CTDI positively correlates with the second current time product.

7. The system of claim 4, wherein the operations further include:
determining a switch time between the two consecutive sub-scans based on the first current time product and the second current time product, wherein the switch time positively correlates with a difference between the first current time product and the second time product.

8. The system of claim 1, wherein the operations further include:
causing the multi-energy CT device to perform the scan according to the scan parameter set and the maximum pitch.

9. The system of claim 8, wherein the performing the scan according to the scan parameter set and the maximum value of the pitch includes:
determining a target pitch based on the maximum pitch and a target scan speed, the target pitch being less than the maximum pitch;
adjusting at least one parameter of the parameter set based on the target pitch and the correlation relationship; and
causing the multi-energy CT device to perform the scan according to the adjusted parameter set and the target pitch.

10. A system for parameter adjustment, comprising:
at least one storage device including a set of instructions; and
at least one processor configured to communicate with the at least one storage device, wherein when executing the set of instructions, the at least one processor is configured to direct the system to perform operations including:

obtaining, by the at least one processor, a parameter correlation set associated with a scan to be performed using a multi-energy computed tomography (CT) device, the parameter correlation set including multiple scanning parameters and multiple reconstruction parameters; and updating, by the at least one processor, at least one parameter of the parameter correlation set;

updating, by the at least one processor, one or more of remaining parameters of the parameter set correlation set based on the updated at least one parameter according to a sufficiency need; and causing, by the at least one processor, the multi-energy CT device to perform the scan according to the updated parameter correlation set.

11. The system of claim 10, wherein
the multi-energy CT device includes a gantry, a collimator, a radiation source, and an isocenter;
the scan to be performed includes a plurality of sub-scans, at least two consecutive sub-scans of the plurality of sub-scans being at different energy levels;
the multiple scanning parameters include a pitch of the multi-energy CT device, a rotation velocity of the gantry, a collimation width of the collimator, a current time product of a sub-scan at an energy level, a switch time between the two consecutive sub-scans, a scan angle of a sub-scan at the energy level, and a distance between the radiation source and the isocenter (SID).

12. The system of claim 11, wherein
the multiple reconstruction parameters include a reconstruction field of view (FOV), a reconstruction range of the reconstruction FOV, a reconstruction center, a reconstruction image thickness, and a reconstruction angle of a sub-scan at the energy level.

13. The system of claim 12, wherein the updating, by the at least one processor, one or more remaining parameters of the parameter set correlation set based on the updated at least one parameter according to a data efficiency need includes:
determining a first distance and a second distance based on the updated at least one parameter and the remaining parameters of the parameter correlation set, wherein the first distance refers to an interval between two consecutive sub-scans with a same energy level, and the second distance refers to a maximum interval between the two consecutive sub-scans with the same energy level; and
updating the one or more of remaining parameters under a condition that the first distance being less than or equal to the second distance.

14. The system of claim 13, wherein the determining a first distance and a second distance based on the updated at least one parameter and the remaining parameters of the parameter correlation set includes:
determining the first distance based on at least one of the scan angle of the sub-scan at the energy level, the pitch, the collimation width of the collimator, the rotation velocity of the gantry, the switch time between the two consecutive sub-scans, and a reconstruction angle of a sub-scan at the energy level; and
determining the second distance based on at least one of the reconstruction FOV, the reconstruction image thickness, the SID, and the collimation width.

15. The system of claim 10, wherein the updating, by the at least one processor, one or more of remaining parameters of the parameter set correlation set based on the updated at least one parameter according to a data efficiency need includes:
updating a pitch of the multi-energy CT device based on the updated at least one parameter according to the data sufficiency need.

16. The system of claim 10, wherein the updating, by the at least one processor, one or more of remaining parameters of the parameter set correlation set based on the updated at least one parameter according to a data efficiency need includes:
updating the one or more of remaining parameters according to at least one of the following:
the pitch negatively correlates with the reconstruction FOV;
the pitch s negatively correlates with the reconstruction image thickness;
the pitch negatively correlates with the reconstruction angle of a sub-scan at an energy level;
the pitch positively correlates with the collimation width;
the pitch negatively correlates with the scan angle of a sub-scan at the energy level;
the pitch positively correlates with the SID;
the pitch negatively correlates with the rotation velocity; or
the pitch negatively correlates with the switch time associated with the two consecutive sub-scans.

17. The system of claim 10, wherein the scan to be performed include a plurality of sub-scans, two consecutive sub-scans of the plurality of sub-scans include a first sub-scan and a second sub-scan, and the at least one processor is further configured to direct the system to perform the operations including:
obtaining a first current time product of the first sub-scan;
obtaining a preset ratio of a first CT dose index (CTDI) of the first sub-scan to a second CTDI of the second sub-scan; and
determining a second current time product of the second sub-scan based on the first current time product and the preset ratio.

18. The system of claim 17, wherein
the first CTDI positively correlates with the first current time product, and
the second CTDI positively correlates with the second current time product.

19. An interface associated with a multi-energy computed tomography (CT) device, comprising:
a protocol selection area, a pitch determination icon, and a scan icon, wherein
the protocol selection area is configured to receive a scan protocol selection instruction for selecting a target scan protocol from a plurality of scan protocols, each of the plurality of scan protocols including a parameter set including multiple scan parameters and multiple reconstruction parameters;
the pitch determination icon is configured to receive a maximum pitch determination instruction for determining a maximum pitch based on a target parameter set of the target scan protocol and a correlation relationship, the correlation relationship describes a correlation between a pitch of the multi-energy CT device and a parameter set of a scan protocol of the multi-energy CT device; and
the scan icon is configured to receive a scan instruction for causing the multi-energy CT device to perform a target scan according to the target scan protocol and the maximum pitch.

20. The interface of claim 19, wherein to receive a scan instruction for causing the multi-energy CT device to perform a target scan according to the target scan protocol and the maximum pitch, the scan icon is further configured to:
determine whether a data sufficiency data need is satisfied;
in response to determining that the data sufficiency need is satisfied, direct the multi-energy CT device to perform the scan; and
in response to determining that the data sufficiency need does not satisfied, adjust one or more parameters of the parameter set and/or the pitch.

* * * * *